(12) United States Patent
Walter et al.

(10) Patent No.: US 8,658,137 B2
(45) Date of Patent: Feb. 25, 2014

(54) INSECTICIDAL COMPOSITIONS AND METHOD FOR INSECT CONTROL

(75) Inventors: James F. Walter, Furlong, PA (US); Reid M. Ipser, Ponchatula, LA (US)

(73) Assignee: FMC Corporation, Philadelphia, PA (US)

( * ) Notice: Subject to any disclaimer, the term of this patent is extended or adjusted under 35 U.S.C. 154(b) by 6 days.

(21) Appl. No.: 13/578,964

(22) PCT Filed: Feb. 23, 2011

(86) PCT No.: PCT/US2011/025849
§ 371 (c)(1),
(2), (4) Date: Aug. 14, 2012

(87) PCT Pub. No.: WO2011/106367
PCT Pub. Date: Sep. 1, 2011

(65) Prior Publication Data
US 2012/0315222 A1    Dec. 13, 2012

Related U.S. Application Data

(60) Provisional application No. 61/307,505, filed on Feb. 24, 2010.

(51) Int. Cl.
*A01N 25/00* (2006.01)
*A01N 65/00* (2009.01)

(52) U.S. Cl.
USPC .......................................... 424/43; 424/770

(58) Field of Classification Search
None
See application file for complete search history.

(56) References Cited

U.S. PATENT DOCUMENTS

| | | | |
|---|---|---|---|
| 6,048,836 A * | 4/2000 | Romano et al. | 510/490 |
| 2005/0244445 A1 | 11/2005 | Anderson | |
| 2006/0029630 A1 | 2/2006 | Overman | |
| 2009/0313883 A1 | 12/2009 | Olson et al. | |

FOREIGN PATENT DOCUMENTS

JP    2001294505 A    10/2001

* cited by examiner

*Primary Examiner* — David J Blanchard
*Assistant Examiner* — Tigabu Kassa
(74) *Attorney, Agent, or Firm* — FMC Corporation

(57) ABSTRACT

An environmentally safe, non-phytotoxic pesticidal composition comprising natural plant oils geraniol and cedar oil and methods of controlling insects is provided.

11 Claims, No Drawings

INSECTICIDAL COMPOSITIONS AND METHOD FOR INSECT CONTROL

FIELD OF THE INVENTION

The present invention relates to pesticidal compositions containing plant essential oils and to methods of controlling insects using essential oils.

BACKGROUND OF THE INVENTION

Insect pests cause significant losses to plants and plant products as well as attack and annoy humans and animals. In household scenarios, insect pests may act as vectors for diseases and allergic matter. Over the years, synthetic chemical pesticides such as synthetic pyrethroids, chlorinated hydrocarbons, organophosphates, carbamates and the like, have provided an effective means of pest control.

However, the public has become increasingly concerned that the widespread use of synthetic chemical pesticides may have caused detrimental environmental effects that are harmful to humans and other animals. For instance, the public has become concerned about the amount of residual chemicals that persist in food, ground water and the environment, and that may be toxic, carcinogenic or otherwise incompatible to humans, domestic animals and/or fish. Moreover, some target pests have even shown an ability to develop resistance to many commonly used synthetic chemical pesticides. In recent times, regulatory guidelines have encouraged a search for potentially less dangerous pesticidal compositions via stringent restrictions on the use of certain synthetic pesticides.

Accordingly, there is a great need for environmentally safe and pesticidally effective compositions that contain no synthetic pyrethroids, chlorinated hydrocarbons, organophosphates, carbamates, and the like, that may be used against insect pests. It would also be advantageous to provide easy to use, inexpensive compositions and methods of using these compositions for controlling these pests that provide the benefits of quick knockdown and eventual mortality of the pests.

SUMMARY OF THE INVENTION

A primary object of the present invention is to provide environmentally safe, non-phytotoxic and pesticidally effective compositions for agriculture or home use against insects. In particular, the present invention provides pesticidal compositions containing natural plant oils that will not harm the environment. Other aspects of the present invention will also be apparent.

DETAILED DESCRIPTION OF THE INVENTION

The present invention provides environmentally safe, non-phytotoxic pesticidal compositions comprising natural plant oils. In particular, the present invention provides a pesticidal concentrate, an aerosol formulation or a Ready-To-Use (RTU) liquid spray composition of the active compounds generiol and cedar oil in admixture with a suitable carrier, a surface active agent and optionally an aerosol propellant.

Use of pesticidal compositions of the present invention generally results in quick knockdown and 100% mortality when compared to the individual components alone. As such, they are advantageously employed as pesticidal agents in uses such as, without limitation, households, agriculture, organic farming, professional pest control, pet bedding, foliage application, seedling box treatment, planting treatment and ornamentals.

A particular embodiment of the present invention is an insecticidal composition comprising:
a) an active ingredient component containing geraniol and cedar oil,
b) a suitable liquid carrier,
c) at least one surface active agent, and
d) optionally an aerosol propellant.

Another embodiment of the present invention is a method for controlling insects comprising applying an insecticidally effective amount of an insecticidal composition comprising:
a) an active ingredient component containing geraniol and cedar oil,
b) a suitable liquid carrier, and
c) at least one surface active agent, to a locus where insect control is needed or expected to be needed.

Geraniol refers to trans-3,7-dimethyl-2,6-octadien-1-ol, CAS number 106-24-1.

Cedar oil, also known as cedar-wood oil, refers to the volatile whole oil extracts derived principally from the heartwood of *Juniperus virginiana* or *Juniperus ashei*. The CAS number for cedar oil is 8000-27-9.

The term "pesticidal concentrate" refers to a mixture of the active ingredients geraniol and cedar oil in a suitable liquid carrier and a surface active agent that requires additional dilution prior to use as a RTU spray or aerosol.

The term "Ready-To-Use liquid spray" as used herein, means a composition of geraniol and cedar oil in a suitable liquid carrier and a surface active agent that can be used without further dilution as a spray delivered by, for example, hand held spray bottles, portable spray tanks, pressurized aerosol spray cans and the like.

It is preferred that the active ingredient geraniol be present in the RTU composition in an amount of from about 0.1% to about 1.0% by weight based on all the components in the total RTU composition, most preferred in an amount of from about 0.4% to about 0.5% by weight based on all the components in the total RTU composition.

It is preferred that the active ingredient cedar oil be present in the RTU composition in an amount of from about 0.01% to about 0.05% by weight based on all the components in the total RTU composition, most preferred in an amount of about 0.02% by weight based on all the components in the total RTU composition.

The term "carrier" as used herein means a liquid material, which may be inorganic or organic and of synthetic or natural origin, with which the active compounds are mixed or formulated to facilitate application of the active ingredients to the locus where insect control is needed. In general, any of the materials customarily employed in formulating pesticides, herbicides, or fungicides, are suitable for use with the present invention. Preferred carriers include, but are not limited to, iso-paraffinic hydrocarbons, $C_1$ to $C_{12}$ straight or branched chain alcohols and water. The most preferred carrier is water. The carrier is present in the RTU composition in an amount that provides the correct dilution of the active ingredients.

The preferred surface active agent is sodium laureth sulfate. It is preferred that the surface active agent is present in the RTU composition in an amount of from about 0.1% to about 1.0% by weight based on all the components in the total RTU composition.

When using a pressurized aerosol spray can to deliver the RTU composition, aerosol propellants such as carbon dioxide, liquefied petroleum gasses, hydrofluorocarbons and known hydrofluorocarbon replacements are particularly useful. Carbon dioxide is the most preferred propellant.

The pesticidal compositions and methods of the present invention are effective against different species of agricultural and household pests and it will be understood that the insects exemplified and evaluated in the working Examples herein are representative of such a wider variety.

The following examples further illustrate the present invention, but, of course, should not be construed as in any way limiting its scope. The examples set forth certain data demonstrating the improved efficacy of the compositions of the present invention.

EXAMPLE 1

Pesticidal Effects of Geraniol, Cedar Oil and Mixtures Thereof

Formulations of geraniol, cedar oil and mixtures thereof were evaluated for contact toxicity against the Lasius ant (*Lasius niger*), lady beetle (*Harmonia axyridis*), brown stink bug (*Halyomorpha halys*), green peach aphid (*Myzus persicae*), house cricket (*Acheta domesticus*) and longtail mealy bug (*Pseudococcus longispinus*). The plant oil test solutions were prepared by dissolving the appropriate amount of the plant oil(s) in deionized water containing 0.5% by weight sodium laureth sulfate, for example 4.4 grams of geraniol was dissolved in 1 liter of deioinized water containing 5 grams of sodium laureth sulfate to prepare a 0.44% test solution of geraniol. Each test solution was poured into a 16 ounce spray can, a valve was installed and the can was charged with carbon dioxide as the propellant. Direct spraying of the test substance onto insects was performed to determine the efficacy of each test solution as follows:

Lasius ant and lady beetle test—In separate tests, ten insects of each species were placed onto an asphalt slab and directly sprayed for 2 seconds with the appropriate test solutions. The time to 100% percent knockdown (insects stopped moving on their own), time for 100% mortality (insects did not respond to probing) and recovery from knockdown was recorded and is summarized in Table 1 below.

Brown stink bug and house cricket test—In separate tests, ten insects of each species were placed onto a concrete slab and directly sprayed for 2 seconds with the appropriate test solutions. The time to 100% percent knockdown (insects stopped moving), time for 100% mortality (insects did not respond to probing) and recovery from knockdown was recorded and is summarized in Table 1 below.

Green peach aphid test—In separate tests, a bell pepper plant, infested with green peach aphids, was sprayed with the appropriate test solution until runoff. The time to 100% percent knockdown (insects stopped moving on their own), time for 100% mortality (insects did not respond to probing) and recovery from knockdown was recorded and is summarized in Table 1 below.

Longtail mealy bug test—In separate tests, ten longtail mealy bugs were established on several leaves of a variegated Euonymus plant, the infested leaves were sprayed with the appropriate test solution until runoff. The percent mortality was assessed after 24 hours and is summarized in Table 1 below.

TABLE 1

Insect Knockdown and Mortality Caused by Test Solutions of Geraniol, Cedar Oil and Mixtures Thereof

| Insect Pest | Test Solution | Time to 100% Knockdown | Time to 100% mortality | Recovery from knockdown |
|---|---|---|---|---|
| Lasius ant | 0.44% geraniol | 9 seconds | 20 seconds | None |
| | 0.02% cedar oil | 29 seconds | No mortality | All recovered |
| | 0.44% geraniol 0.02% cedar oil | 4 seconds | 9 seconds | None |
| Lady beetle | 0.44% geraniol | 20 seconds | 60 seconds | None |
| | 0.02% cedar oil | 30 seconds | No mortality | All recovered |
| | 0.44% geraniol 0.02% cedar oil | 10 seconds | 30 seconds | None |
| Brown stink bug | 0.44% geraniol | 20 seconds | 90 seconds | None |
| | 0.02% cedar oil | 60 seconds | No mortality | All recovered |
| | 0.44% geraniol 0.02% cedar oil | 15 seconds | 30 seconds | None |
| Green peach aphid | 0.44% geraniol | No apparent knockdown | 3 hours | None |
| | 0.02% cedar oil | No apparent knockdown | No mortality | All recovered |
| | 0.44% geraniol 0.02% cedar oil | 30 seconds | 1 hour | None |
| House cricket | 0.44% geraniol | 60 seconds | 3 hours | None |
| | 0.02% cedar oil | No apparent knockdown | No mortality | All recovered |
| | 0.44% geraniol 0.02% cedar oil | 30 seconds | 25 minutes | None |
| Longtail mealy bug | 0.44% geraniol | Not Determined | 50% mortality at 24 hours | Not Determined |
| | 0.02% cedar oil | Not Determined | 0% mortality at 24 hours | Not Determined |
| | 0.44% geraniol 0.02% cedar oil | Not Determined | 100% mortality at 24 hours | Not Determined |

These data demonstrate that cedar oil added to geraniol provides a synergistic composition that greatly improves the time to knockdown and quickness to 100% mortality of insects as compared to the individual components and that overall, geraniol and cedar oil mixtures can be used as a safe and effective alternative pesticide for control of household pests.

Those of ordinary skill in the art will appreciate that variations of the invention may be used and that it is intended that the invention may be practiced otherwise than as specifically described herein. Accordingly, this invention includes all modifications encompassed within the spirit and scope of the invention as defined by the following claims.

What is claimed is:

1. An insecticidal composition consisting of:
    a) active ingredients geraniol and cedar oil,
    b) a suitable liquid carrier, and
    c) a surface active agent, and
    d) optionally an aerosol propellant.

2. The composition of claim 1 wherein the suitable liquid carrier is water.

3. The composition of claim 1 wherein the surface active agent is sodium laureth sulfate.

4. The composition of claim 1 wherein the geraniol is present in an amount of from about 0.1% to about 1.0% by weight based on all the components in the total composition and the cedar oil is present in an amount of from about 0.01% to about 0.05% by weight based on all the components in the total composition.

5. The composition of claim 4 wherein the geraniol is present in the amount of about 0.44% by weight based on all the components in the total composition and the cedar oil is present in the amount of about 0.02% by weight based on all the components in the total composition.

6. A method for controlling insects comprising applying an insecticidally effective amount of a composition consisting of:
    a) active ingredients geraniol and cedar oil,
    b) a suitable liquid carrier, and
    c) a surface active agent, and
    d) optionally an aerosol propellant
    to a locus where insect control is needed or expected to be needed.

7. The method of claim 6 wherein the suitable liquid carrier is water.

8. The method of claim 6 wherein the surface active agent is sodium laureth sulfate.

9. The method of claim 6 wherein the geraniol is present in an amount of from about 0.1% to about 1.0% by weight based on all the components in the total composition and the cedar oil is present in an amount of from about 0.01% to about 0.05% by weight based on all the components in the total composition.

10. The method of claim 9 wherein the geraniol is present in the amount of about 0.44% by weight based on all the components in the total composition and the cedar oil is present in the amount of about 0.02% by weight based on all the components in the total composition.

11. The method of claim 6 wherein the aerosol propellant is added to the composition.

* * * * *